United States Patent [19]

Mosbach et al.

[11] 4,371,528
[45] Feb. 1, 1983

[54] CONTROLLING MICRO-ORGANISMS

[76] Inventors: Erwin H. Mosbach, 300 Central Park West, New York, N.Y. 10024; Charles K. McSherry, 10 Nathan D.Perlman Pl., New York, N.Y. 10003; Phillip B. Hylemon, MCV Station, Richmond, Va. 23298

[21] Appl. No.: 360,708

[22] Filed: Mar. 22, 1982

[51] Int. Cl.$^3$ .............................................. A61K 31/58
[52] U.S. Cl. .................................. 424/241; 260/239.5
[58] Field of Search ..................... 424/241; 260/239.57

[56] References Cited

PUBLICATIONS

Ayengar et al., "Steroids" vol. 38, No. 3, Sep. 1981, pp. 333-345.

Primary Examiner—Elbert L. Roberts

[57] ABSTRACT

A method of controlling microorganisms which comprises contacting said microorganisms with a small but effective amount of a compound of the formula,

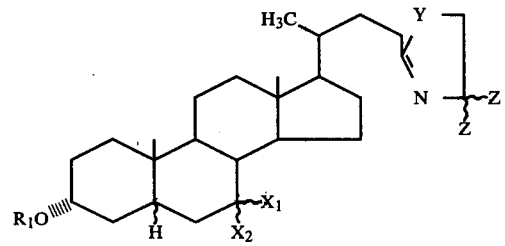

wherein $R_1$ is H or acyl; $X_2$ is H, OH, acyloxy, aryl, aralkyl, aryloxy, lower alkyl or lower alkoxy; $X_1$ is H, OH or acyloxy; provided that when $X_2$ is OH, acyloxy, lower alkoxy, or aryloxy; $X_1$ is H or lower alkyl; and when taken together $X_1$ and $X_2$ are oxo (O=); Y is S, N, or O; each Z is H, OH, lower alkyl, aryl, aralkyl, substituted lower alkyl, cycloalkyl and substituted aryl; and the non-toxic pharmaceutically acceptable salts thereof.

4 Claims, No Drawings

CONTROLLING MICRO-ORGANISMS

The invention described herein was made in the course of work done under a grant from the U.S. Department of Health and Human Services and certain rights thereto have been retained by and for the benefit of the U.S. Government.

This invention relates to and has as its objective the method of controlling the growth of various microorganisms. More particularly, this invention relates to and has as its objective, the method of controlling various faculative and anaerobic microorganisms, which comprises subjecting said microorganisms to the action of small but effective amounts of a compound of the formula:

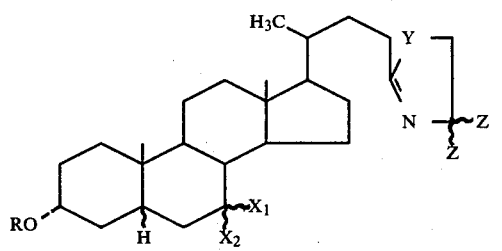

where R is H or acyl; $X_2$ is H, OH, acyloxy, aryl, aralkyl, aryloxy, lower alkyl or lower alkoxy; $X_1$ is H, OH or acyloxy; provided that when $X_2$ is OH, acyloxy, lower alkoxy or aryloxy, $X_1$ is H or lower alkyl; and when taken together $X_1$ and $X_2$ are oxo (O=); Y is S, N, or O; each Z is H, OH, lower alkyl, aryl, aralkyl, substituted-lower alkyl, cycloalkyl and substituted aryl; and the non-toxic, pharmaceutically acceptable salts thereof.

Even more specifically, this invention relates to and has as its objective the control of various faculative and anaerobic bacterium by subjecting said bacterium to the action of a compound of the formula,

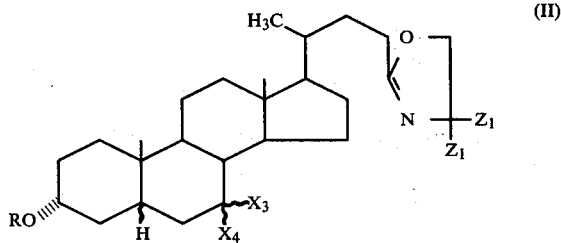

wherein R is H or acyl; $X_3$ is H, OH or lower alkyl; $X_4$ is H, OH, acyloxy, lower alkyl or lower alkoxy; provided that when $X_4$ is OH, acyloxy or lower alkoxy, $X_3$ is not OH; and taken together $X_3$ and $X_4$ are oxo (O=); each $Z_1$ is H or lower alkyl; and the non-toxic, pharmaceutically acceptable salts thereof.

The anti-microbial compounds which may be employed in the practice of the instant invention are known in the art and may be prepared by the skilled worker in accordance with the teachings and disclosures of Ayengar, et al., Steroids, 38: pp 333–345 (1981) and those contained in United States Patent Application Ser. No. 294,338, filed Aug. 19, 1981.

The microorganisms which may be controlled by the practice of the instant invention are faculative and anaerobic microorganisms, including such microorganisms as faculative and anaerobic bacteria. Among the bacteria which may be controlled by the practice of this invention may be included gram negative and gram positive bacteria such as Eubacteria, for example, *Eubacterium aerofaciens, Eubacterium species*, VPI 12708 (Virginia Polytechnic Institute Collection); Clostridium, such as *Clostridium difficile, Clostridium sordellii* (VPI 11801); Bacteroides, for example, *Bacteroides distasonis* (VPI 4243), *Bacteroides vulgatus* (VPI 4245), *Bacteroides fragilis* (VPI 2393), *Bacteroides thetaiotaomicrons* (VPI 5482), *Bacteroides ovatus* (VPI 3524) and Salmonella, for example, *Salmonella typhimurium* TA 100. Other microorganisms may also be controlled by the practice of this invention.

We have also discovered that this invention may be satisfactorily practiced by subjecting the microorganisms sought to be controlled to a small but effective amount of the compounds to be employed herein. The skilled worker will readily be able to determine the amount of each compound to be employed herein in accordance with the nature and character of the microorganism sought to be controlled and the patient sought to be treated. It is understood that when treating a patient suffering from a pathologic condition caused by the microorganisms to be controlled by the practice of the instant invention the route of administering the compounds employed herein is of importance in determining the amount of the compound to be employed. In order to obtain the satisfactory results from the instant invention it will be necessary to administer the compounds of the instant invention to the patient being treated by a systemic route, for example, perorally, or parenterally. The compositions employed for such purposes should contain the compounds of this invention in a suitable systemically administerable, pharmaceutically acceptable composition, all as is well known to the skilled worker. Thus, suitable injectable compositions, orally administerable pills, capsules or elixirs or other suitable, pharmaceutically acceptable compositions containing the active compounds of this invention may be employed in the practice thereof. The skilled worker is well equipped to determine the most suitable compositions and dosage forms to be employed in the practice of the instant invention.

The acyl moieties which may be employed in the practice of this invention include those acyl groups which are derived from hydrocarbon carboxylic acids of twelve carbon atoms or less and include such acids as the alkanoic, cycloalkanoic, monocyclic acyl and monocyclic aralkyl acids.

The instant invention may be further illustrated by the following Examples.

EXAMPLE 1

Eubacterium sp. VPI 12708 was isolated from the feces of colon cancer patients and characterized at the VPI Anaerobe Laboratory. This bacteria were then cultured anaerobically under an argon gas atmosphere in a modified (2 gm fructose/liter) Brain Heart Infusion (Difco) medium in accordance with the procedures set forth and described by White, et al., "Bile Acid Induction Specificity of 7-Dehydroxylace Activity in an Intestinal Eubacterium Species", Steroids 35: pp 103–109 (1980). Bacterial growth was monitored by measuring culture turbidity with a Klett-Summerson colorimeter (No. 66 filter). Compounds of the instant invention, as set forth in Table 1 below, were dissolved in methanol and added in varying concentrations of from 0.01 to 0.1 mM to 5 ml. of growing cultures at 40 to 70 Klett Units. Turbidity was determined before addition of the test compound and at various time points thereafter. Cultures were incubated at 37° C. under an argon gas atmosphere in rubber-stoppered tubes. Control samples were run concurrently with the same volume of methanol, but without the test compounds. Samples of the incubated cultures were anaerobically removed at points along the growth curve, diluted to $10^{-1}$, $10^{-2}$ and $10^{-3}$, in basal salts medium under anaerobic conditions, in accordance with the procedures set forth by Holdeman et al., Anaerobe Laboratory Manual, 4th Edition, Anaerobe Laboratory, Virginia Polytechnic Institute and State University, Blacksburg, Va. (1977). Cells were placed on Brain Heart Infusion agar plates and viable counts determined after 48 hours of anaerobic incubation. Observations of turbidity and direct microscopic observations of bacterial cells at various times after addition of the test compounds were made and reduction in viable counts correlated with a decrease in turbidity.

The foregoing procedures were also followed with a number of other bacterial species and the results obtained are reported in Table 1 below.

TABLE 1

| Microorganism | Compounds* | | | |
|---|---|---|---|---|
| | 1 | 2 | 3 | Control |
| Eubacterium sp. VPI 12708 | S | S | R | R |
| Eubacterium aerofacien | S | — | S | R |
| Clostridium sordellii VPI 11801 | S | S | R | R |
| Clostridium difficile | S | S | S | R |
| Bacteroides distasonis VPI 4343 | S | S | S | R |
| Bacteroides vulgatus | S | S | S | R |
| Bacteroides fragilis VPI 2393 | S | S | S | R |
| Bacteroides thetaiotaomicron VPI5482 | S | S | S | R |
| Bacteroides ovatus VPI 3524 | S | S | S | R |
| Pseudomonas aeruginosa | R | — | — | R |

TABLE 1-continued

| Microorganism | Compounds* | | | |
|---|---|---|---|---|
| | 1 | 2 | 3 | Control |
| Samonella typhimurium TA 100 | S | S | R | R |

*Compounds of Formula II
1 = R=X$_1$=H; X$_2$=αOH; Z$_1$=CH$_3$; (Conc. 0.025 mM)
2 = R$_1$=H; X$_1$=Z$_1$=CH$_3$; X$_2$=αOH (Conc. 0.025 mM)
3 = R$_1$=X$_1$=X$_2$=H; Z$_1$=CH$_3$ (Conc. 0.025 mM)
R = Resistant, no effect on growth
S = Sensitive, (bacteriolysis or severe inhibition of growth)

These results demonstrate that the test bacteria are controlled when subjected to the action of small amounts of the compounds of the instant invention.

When in the formulae appearing in this Specification and the Claims appended thereto a curved line ( $\{$ ) is employed, it is meant to denote that the moiety connected thereby may be in the alpha- or beta-stereochemical position, as the case may be.

This invention may be variously otherwise encompassed within the scope of the appended claims.

What is claimed is:

1. The method of controlling microorganisms, which comprises subjecting said microorganisms to the action of a small but effective amount of a compound of the formula,

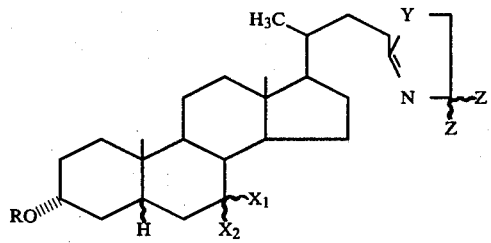

wherein R is H or acyl; Y is N, O or S; each Z is H, lower alkyl, OH, aryl, arakyl, substituted-lower alkyl cycloalkyl or substituted acyl; X$_1$ is H, OH, acyloxy, alkyl or aryl; X$_2$ is H, OH, acyloxy, alkyl, aryl, alkoxy, aryloxy, or aralkyl; X$_1$ and X$_2$ when taken together is oxo (O=); and the non-toxic, pharmaceutically acceptable salts thereof.

2. The method of claim 1 wherein Y is O; each Z is lower alkyl; X$_1$ is H; R is H and X$_2$ is OH.

3. The method of claim 1 wherein Y is O; each Z is lower alkyl; R is H; X$_1$ is lower alkyl and X$_2$ is OH.

4. The method of claim 1 wherein the microorganisms are faculative or anaerobic bacteria.

* * * * *